(12) United States Patent
Michaels

(10) Patent No.: US 10,299,971 B2
(45) Date of Patent: May 28, 2019

(54) LIFESAVING KIT

(71) Applicant: Iman Ramzy Michaels, Cleveland, OH (US)

(72) Inventor: Iman Ramzy Michaels, Cleveland, OH (US)

(*) Notice: Subject to any disclaimer, the term of this patent is extended or adjusted under 35 U.S.C. 154(b) by 355 days.

(21) Appl. No.: 15/202,828

(22) Filed: Jul. 6, 2016

(65) Prior Publication Data
US 2016/0367413 A1 Dec. 22, 2016

Related U.S. Application Data

(63) Continuation of application No. 13/757,761, filed on Apr. 23, 2013, now abandoned.

(51) Int. Cl.
| | |
|---|---|
| *B65D 69/00* | (2006.01) |
| *A61F 17/00* | (2006.01) |
| *A61B 50/30* | (2016.01) |
| *A61K 9/00* | (2006.01) |
| *A61K 31/137* | (2006.01) |
| *A61K 31/616* | (2006.01) |
| *A61K 31/7004* | (2006.01) |
| *G09B 5/12* | (2006.01) |
| *G09B 19/24* | (2006.01) |
| *A61B 50/00* | (2016.01) |

(52) U.S. Cl.
CPC .............. *A61F 17/00* (2013.01); *A61B 50/30* (2016.02); *A61K 9/0019* (2013.01); *A61K 31/137* (2013.01); *A61K 31/616* (2013.01); *A61K 31/7004* (2013.01); *G09B 5/125* (2013.01); *G09B 19/24* (2013.01); *A61B 2050/005* (2016.02); *A61B 2050/3008* (2016.02)

(58) Field of Classification Search
CPC ... A45C 11/24; A61F 17/00; A61B 2050/005; A61B 2050/3008; A61J 1/03; A61J 7/0418; A61J 7/0454
USPC ................. 206/38, 320, 570, 572, 538, 539; 361/679.55, 679.57; 455/344, 575.1, 455/575.8
See application file for complete search history.

(56) References Cited

U.S. PATENT DOCUMENTS

| | | | | |
|---|---|---|---|---|
| 3,179,891 A | * | 4/1965 | Sharma ................ | G04B 47/006 206/235 |
| 7,431,161 B2 | * | 10/2008 | Carlino ................. | B65D 69/00 132/316 |
| 8,055,380 B1 | * | 11/2011 | Verma ................... | A61J 7/0481 221/115 |
| 8,193,918 B1 | * | 6/2012 | Shavelsky ................ | A61J 7/04 340/309.16 |
| 8,833,379 B1 | * | 9/2014 | Kaplan ................. | A45D 33/26 132/287 |
| 2002/0050462 A1 | * | 5/2002 | Penney ................ | A61M 5/002 206/363 |

(Continued)

*Primary Examiner* — Luan K Bui
(74) *Attorney, Agent, or Firm* — Tarolli, Sundheim, Covell & Tummino LLP

(57) ABSTRACT

A lifesaving kit is disclosed. The kit includes a body that can be attached to a cellular phone. A compartment is disposed on the body and contains an article of medical paraphernalia. The compartment has a closed condition and an open condition. An electronics system is configured to provide instructions on how to utilize the medical paraphernalia. A method of using the lifesaving kit is also disclosed.

11 Claims, 9 Drawing Sheets

(56) References Cited

U.S. PATENT DOCUMENTS

| | | | |
|---|---|---|---|
| 2012/0160716 A1* | 6/2012 | Chan | A61J 7/0481 206/216 |
| 2013/0119096 A1* | 5/2013 | Morgan | A45F 3/005 224/148.1 |
| 2013/0189944 A1* | 7/2013 | McCoy | G16H 10/20 455/404.1 |
| 2013/0292294 A1* | 11/2013 | Wilson | A61F 17/00 206/571 |

* cited by examiner

LIFESAVING KIT

RELATED APPLICATIONS

This application is a continuation of U.S. patent application Ser. No. 13/757,761 filed Apr. 23, 2013 entitled THE GOOD SAMARITAN A DIGITAL LIFESAVING KIT, the entirety of which is hereby incorporated by reference for all purposes.

TECHNICAL FIELD

The present disclosure relates to a medical device, and more particularly to a medical kit that provides instructions to an operator on how to administer medical aid.

BACKGROUND

Emergency and medical personnel can be summoned in the United States to respond to an emergency situation by dialing "9-1-1" from any telephone. Although every effort is taken to minimize response time to the emergency situation, an appreciable amount of time may pass between the moment the initial call is made and when the emergency and medical personnel actually arrive at the scene of the emergency situation. The treatment window for certain health conditions (e.g., stroke) can be very small and it can be important to immediately administer medical aid while waiting for the emergency and medical personnel. However, the average person may not be knowledgeable about how to respond to various emergency situations.

Therefore, what is needed is a system that can help the average person administer medical aid while waiting for the arrival of emergency and medical personnel.

SUMMARY

One aspect of the present disclosure relates to an apparatus for providing medical aid. The apparatus includes a body configured to be attached to a cellular phone. At least one compartment is disposed on the body and contains at least one article of medical paraphernalia. The at least one compartment has a closed condition and an open condition. An electronics system is configured to provide instructions on how to utilize the at least one article of medical paraphernalia.

Another aspect of the present disclosure relates to a method for providing medical aid. The method includes the step of providing a kit that is attachable to a cellular phone and includes an article of medical paraphernalia stored in a compartment. The kit further includes an electronics system that is configured to provide instructions on how to utilize the at least one article of medical paraphernalia. The method further includes the steps of identifying a medical emergency, contacting emergency services, activating the kit, retrieving the article of medical paraphernalia from the compartment, providing instructions through the electronics system, and administering medical aid by following the instructions.

BRIEF DESCRIPTION OF THE DRAWINGS

The foregoing and other features and advantages of the present disclosure will become apparent to those skilled in the art to which the present disclosure relates upon reading the following description with reference to the accompanying drawings, in which.

DETAILED DESCRIPTION

Definitions

Figure 1:
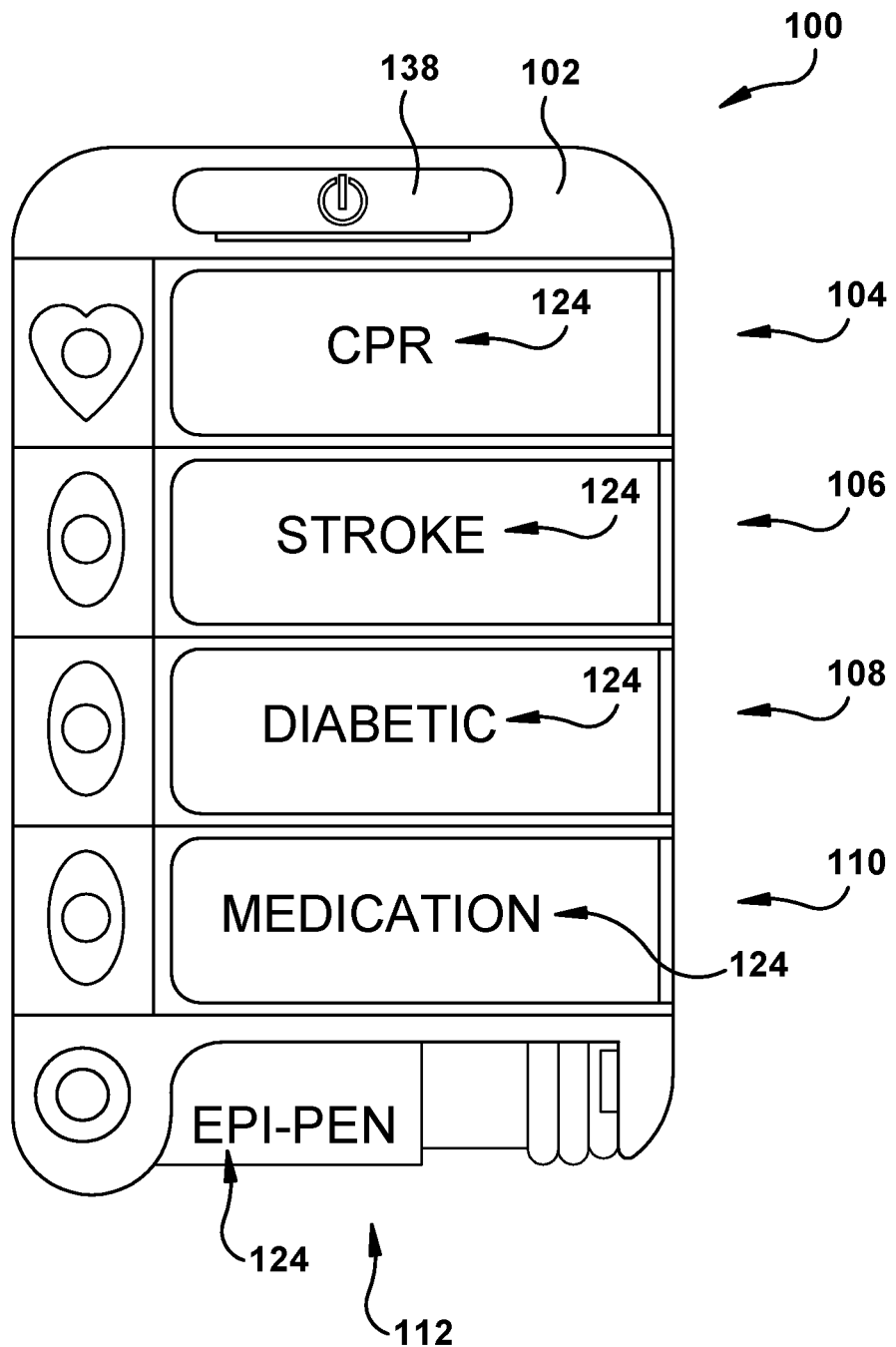
FIG. 1 is a plan view of a lifesaving kit constructed in accordance with one aspect of the present disclosure.
Figure 2:
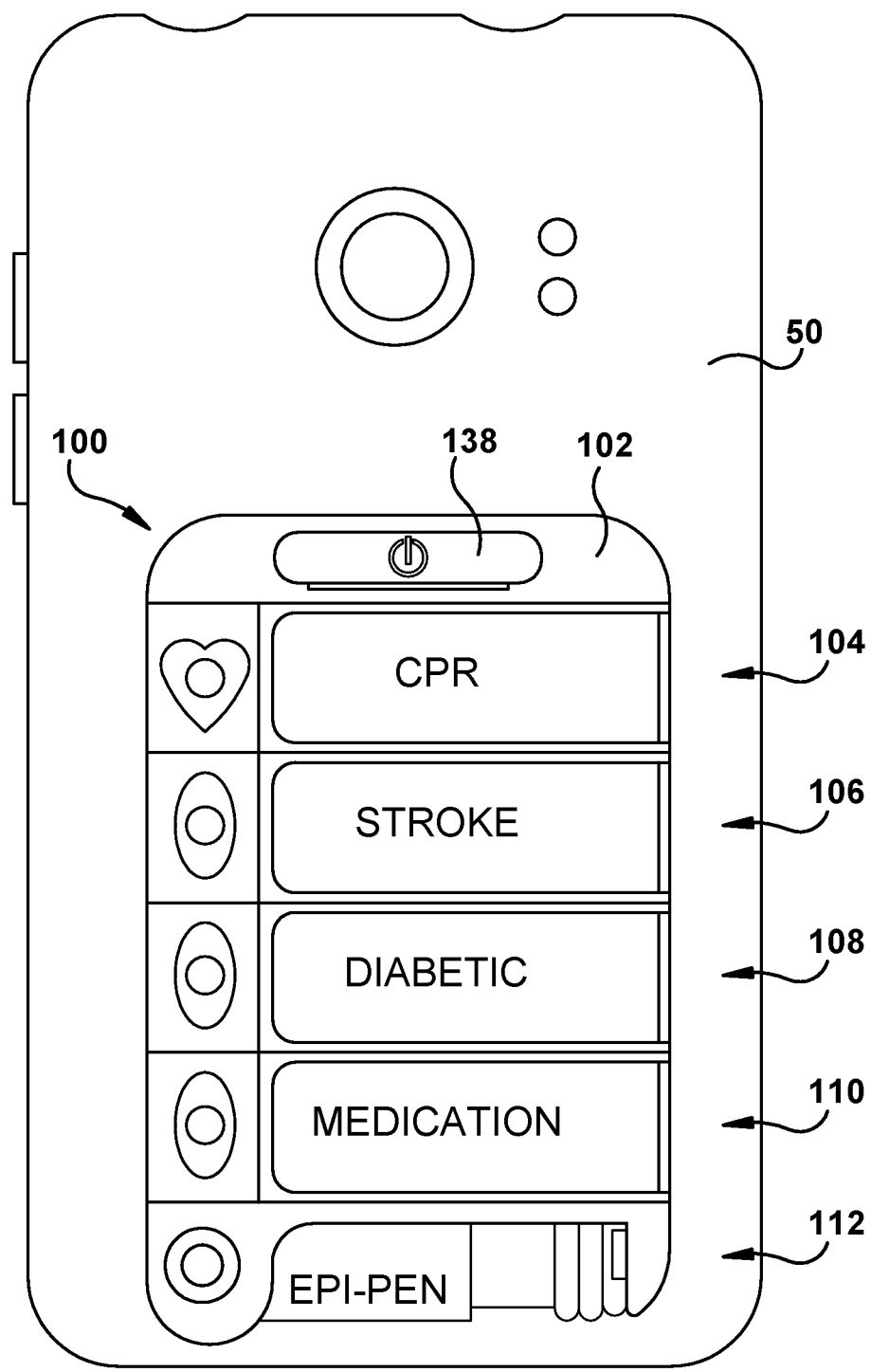
FIG. 2 is a view of the kit of FIG. 1 mounted to a cellular phone.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

System

Referring to FIGS. 1-4 a lifesaving kit 100 according to one example embodiment is shown. The kit 100 includes a substantially rectangular shaped body 102 with five compartments 104, 106, 108, 110, 112. In one aspect, the body 102 is adapted to be secured to an external surface of a cellular phone 50 (see FIG. 2). However, it will be appreciated that the body 102 can be integrally formed into the external case of the cellular phone. The 102 body can be any other suitable shape, although it is preferable for the body 102 to substantially mimic the overall shape of the cellular phone 50 so as to avoid adding unnecessary bulk to the cellular phone 50.

The five compartments 104, 106, 108, 110, 112 are spaced along a longitudinal axis of the body 102. Each of the compartments 104, 106, 108, 110, 112 is substantially cuboid shaped and extends substantially perpendicular to the longitudinal axis. It will be appreciated that fewer or greater compartments can be provided. Additionally, it will be appreciated that each compartment can have any other suitable shape that allows the compartment to contain desired medical paraphernalia. The compartments can be replaceable such that each compartment can be removed from the body 102 and replaced with a new compartment once the contents of the original compartment has been used. Each of the compartments 104, 106, 108, 110, 112 is provided with a cover 114, 116, 118, 120, 122 that selectively closes the respective compartment. In the example embodiment each of the covers 114, 116, 118, 120, 122 is pivotably attached to the body 102. However, the covers can have any other suitable connection mechanism that allows for closure of the respective compartment. For example, the covers can be slidably attached to the body, be manufactured out of a frangible material that allows the cover to be broken, or be connected by perforations that allow the entire cover to be detached from the body. The medical paraphernalia can be pivotably attached to the body for movement between an undeployed condition and a deployed condition, as is the case with the epinephrine pen (discussed below). Each of the covers 114, 116, 118, 120, 122 is provided with indicia 124 that identify the contents of the respective compartment 104, 106, 108, 110, 112. The indicia 124 can be words, letters, numbers, symbols, or any other suitable marking.

Figure 3:
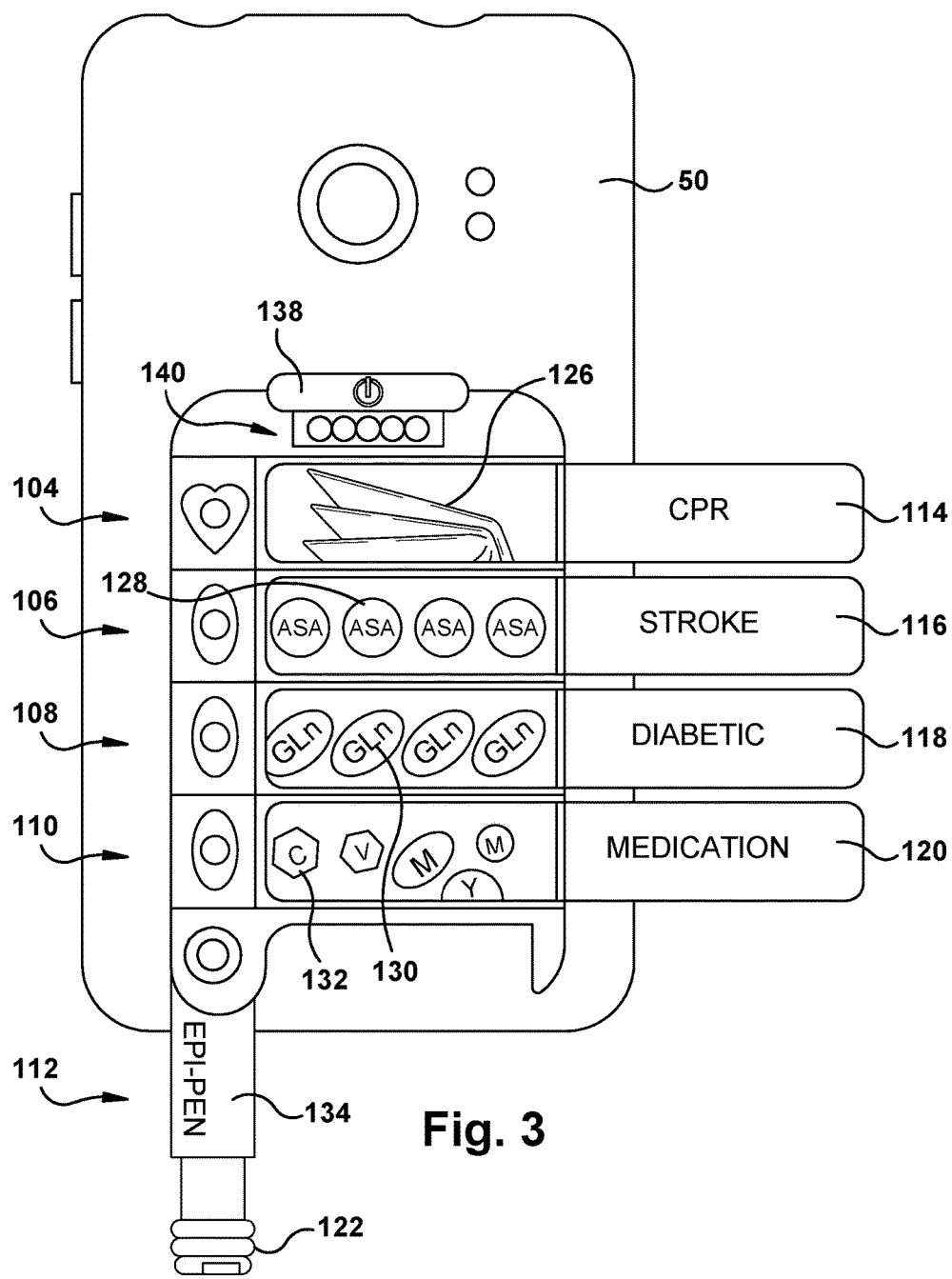
FIG. 3 is a view of the kit of FIG. 1 with compartments open to show the contents contained therein.
Figure 4:
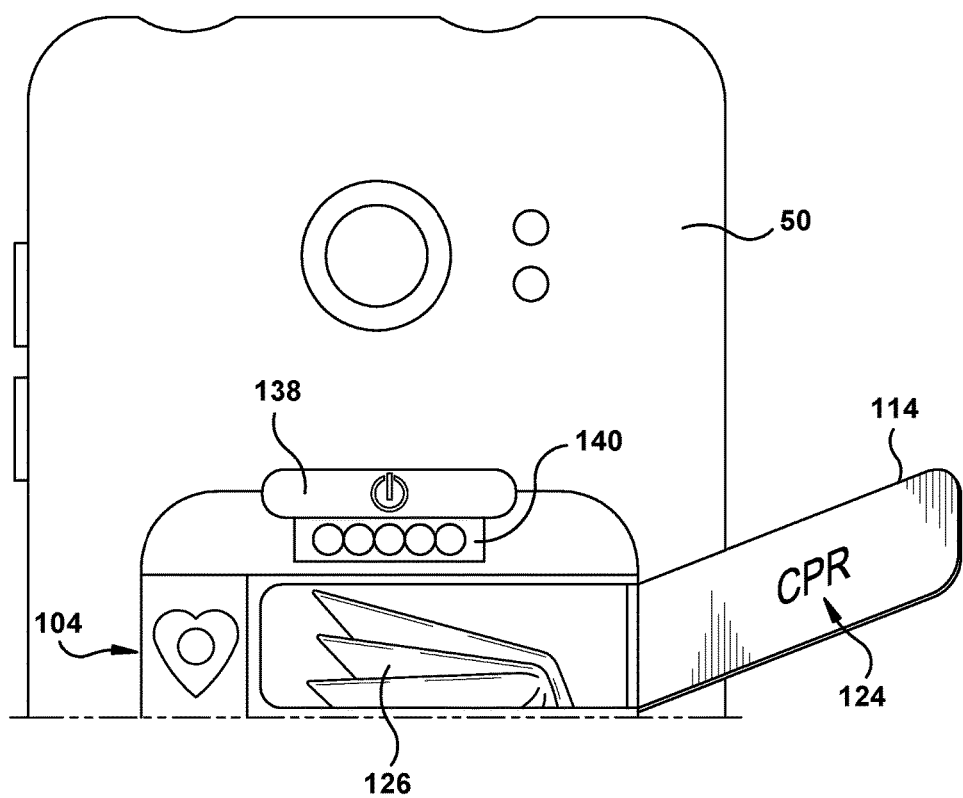
FIG. 4 is a detail view of part of the kit of FIG. 1 focusing on a single compartment.

Each of the compartments 104, 106, 108, 110, 112 contain medical paraphernalia that can be used to administer medical aid to a patient experiencing a medical emergency. In the example embodiment the first compartment 104 contains a disposable plastic mouth guard 126 that can be used when performing the cardiopulmonary resuscitation technique. The second compartment 106 contains aspirin 128 that can be given to a patient that is showing signs of a suspected stroke or heart attack. The third compartment 108 contains glucose packets 130 that can be given to a patient that is showing signs of low glucose levels. The fourth compartment 110 is provided for storing any personal medications 132, vitamins, etc. that are taken by the owner of the cellular phone 50 to which the lifesaving kit 100 is attached. The fifth compartment 112 stores an epinephrine pen 134 that can be used on a patient showing signs of an allergic reaction that compromises the air pathway. The epinephrine pen 134 is pivotably attached to the body 102 for pivotable movement between an undeployed condition (FIG. 1) and a deployed condition (FIG. 3). In the undeployed condition the epinephrine pen 132 is positioned such that there exists no chance of the epinephrine pen being administered (i.e., the needle of the epinephrine pen is covered). In the deployed condition the epinephrine pen 132 is positioned such that the epinephrine pen can be administered (i.e., the needle of the epinephrine pen is exposed). Each of the compartments 104, 106, 108, 110, 112 can be provided with sensors 136 (see FIG. 8) that sense when a particular compartment is opened. Although the example embodiment is arranged for the compartments to contain a mouth guard, aspirin, glucose packets, and an epinephrine pen, it will be appreciated that the compartments can be stocked with any other desired medical paraphernalia.

The body 102 is further provided with a power button 138 and a speaker 140. The power button 138 is arranged to conceal the speaker 140 when the kit 100 is inactive. The power button 138 can be depressed to actuate the lifesaving kit 100 to provide instructions on how to administer aid once one of the compartments 104, 106, 108, 110, 112 is opened by an operator. The power button 138 is configured such that depressing the power button 138 causes the power button 138 to move relative to the body 102 to reveal the speaker 140. It will be appreciated that the power button 138 can be provided adjacent to the speaker 140 such that the speaker 140 is always revealed. Additionally, it will be appreciated that the speaker 140 can be replaced with a display that shows written text, pictographs, etc. that instruct an operator how to administer aid.

Figure 8:
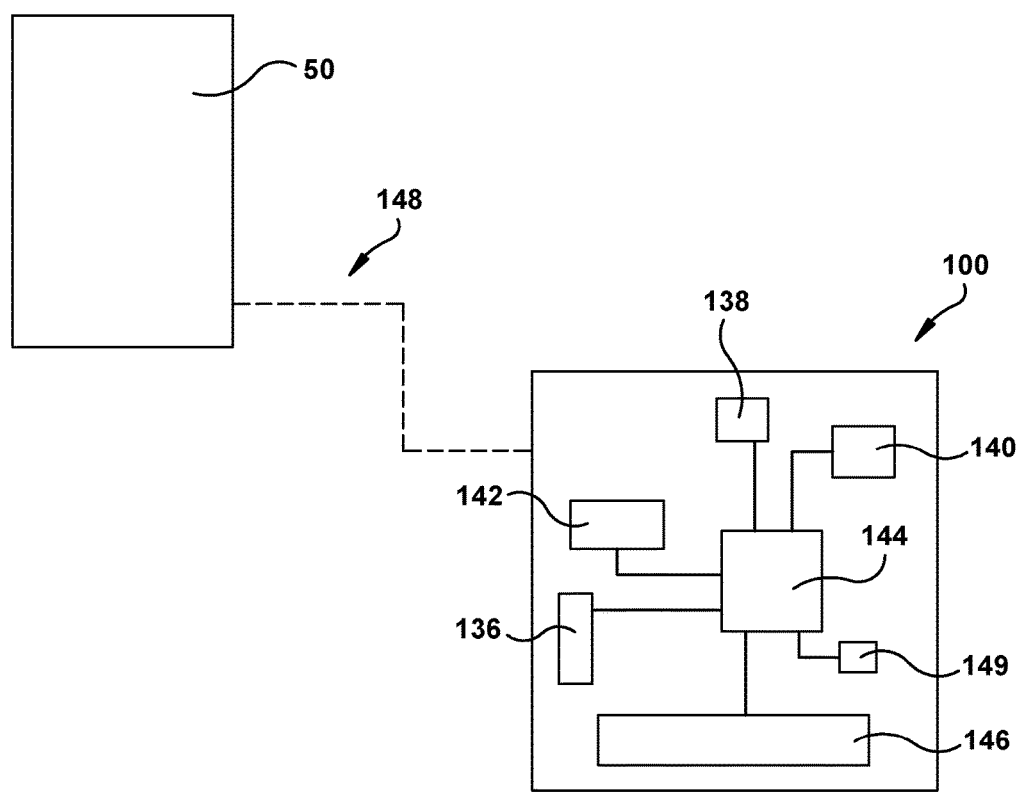
FIG. 8 is a schematic view of electrical components of the kit of FIG. 1.

Referring to FIG. 8, various electrical components of the lifesaving kit 100 are schematically shown. Additionally, communication between various electrical components of the kit 100, as well as the communication between the kit 100 and the cellular phone 50 is also schematically shown. The lifesaving kit 100 includes instructions that are saved on an electronic memory 142. The instructions relate to using the contents of the compartments 104, 106, 108, 110, 112 to administer aid to a patient suffering from a medical emergency. A central processing unit 144 is in communication with the electronic memory 142. The central processing unit 144 retrieves a particular set of instructions from the electronic memory 142 based on which of the compartments 104, 106, 108, 110, 112 is opened as determined by the sensors 136. The central processing 144 unit relays the instructions to the speaker 140. The speaker 140 transforms the instructions into a corresponding auditory instruction that can be heard by an operator. The kit 100 includes a power source 146 that provides electrical power to the electrical components. A communication line 148 is provided for providing communication between the lifesaving kit 100 and the cellular phone 50. The communication line 148 can be a hard line connection or a wireless connection. The lifesaving kit 100 can also include a programmable alarm 149 that provides an hourly, daily, etc. reminder of when to take the personal medications 132 stored in the fourth compartment 110. It will be appreciated that other electrical arrangements can be provided. For example, the lifesaving kit 100 can be arranged such that power source of the cellular phone provides electrical power to the lifesaving kit 100. As another example, the lifesaving kit 100 can be arranged such that the lifesaving kit uses the speaker of the cellular phone to provide the auditory instructions to the operator. As yet another example, the lifesaving kit 100 can be arranged such that the instructions are stored on the electronic memory of the cellular phone. As yet even another example, the lifesaving kit 100 can be arranged such that the instructions are retrieved from the Internet upon activation of the kit.

Figure 5:
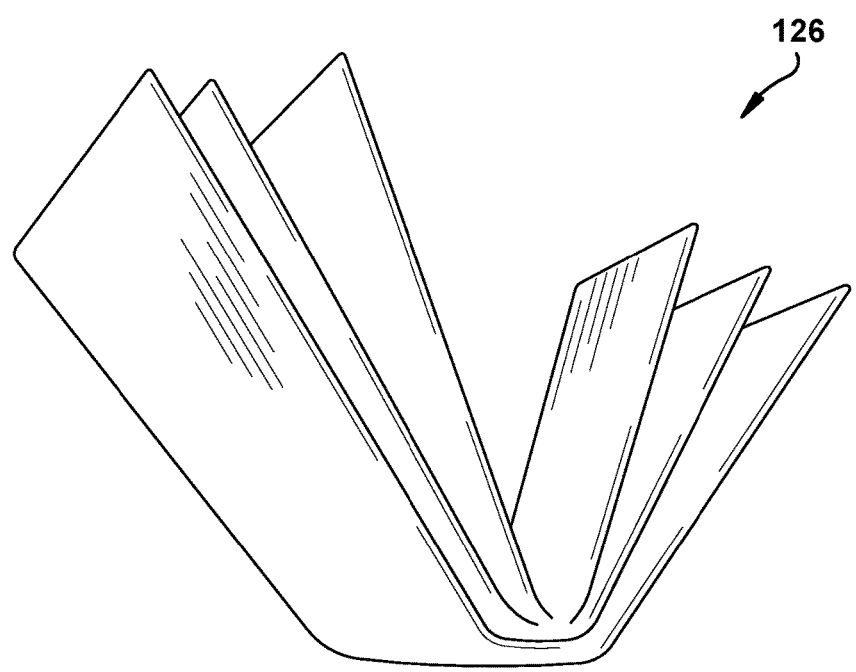
FIG. 5 is a perspective view of a plastic mouth guard in a folded condition.
Figure 6:
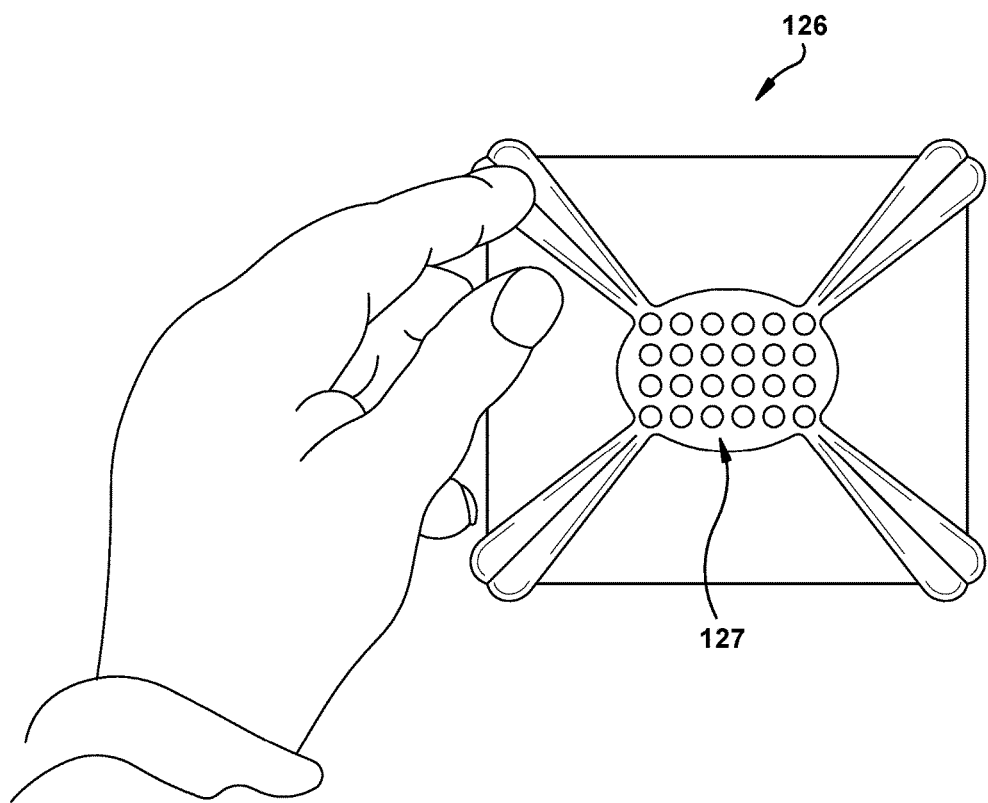
FIG. 6 is a perspective view of the plastic mouth guard of FIG. 5 in an unfolded condition.
Figure 7:
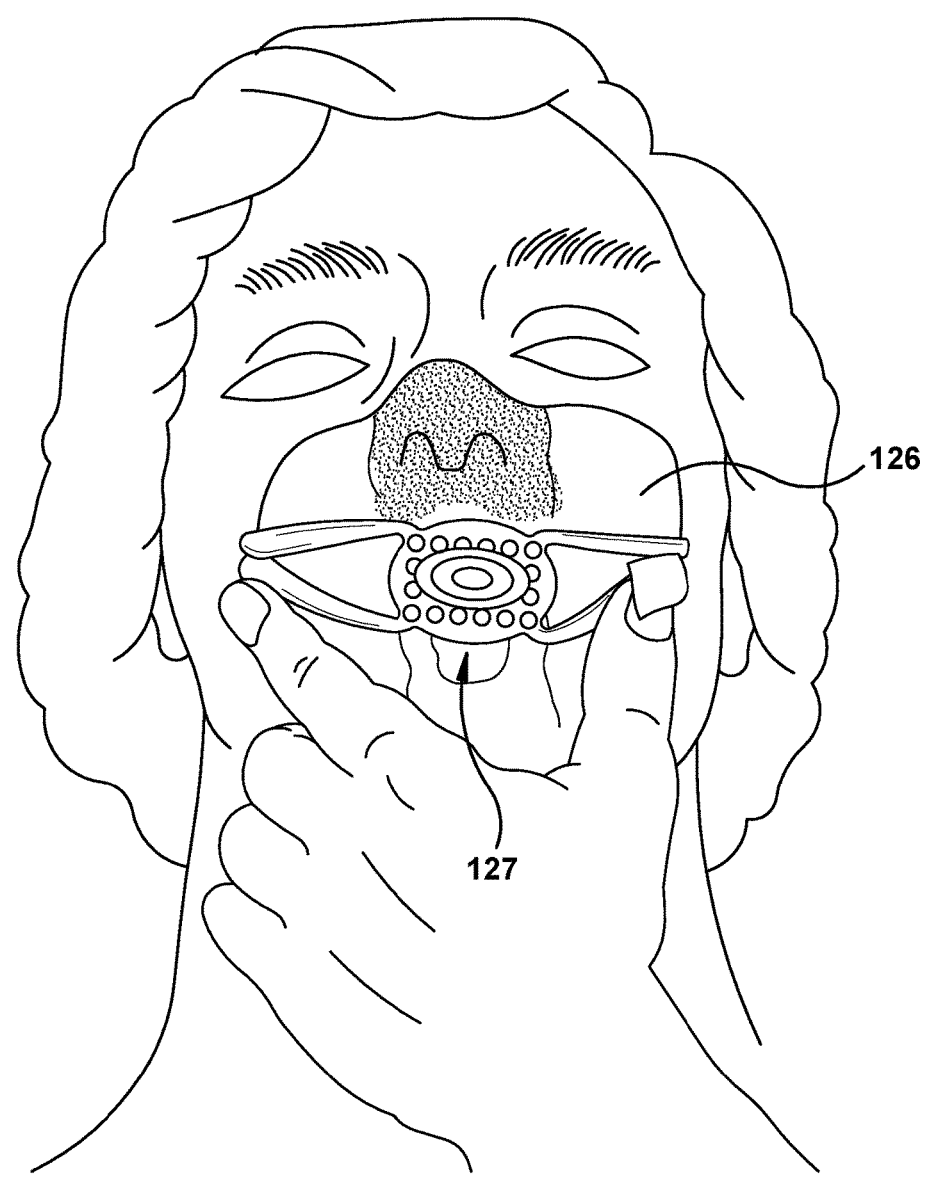
FIG. 7 is a view of the plastic mouth guard of FIG. 5 being used on a patient.

Referring to FIGS. 5-7, the disposable plastic mouth guard 126 provided in the first compartment 104 is shown. The mouth guard 126 has a folded configuration (FIG. 5) and an unfolded configuration (FIG. 6). The mouth guard 126 is provided with a plurality of centrally located apertures 127. In use, the mouth guard 126 is removed from the first compartment 104 and manipulated to the unfolded configuration. Then, the unfolded mouth guard 126 is placed flat against the mouth of the patient requiring CPR such that the apertures 127 are aligned with the mouth of the CPR recipient. CPR can then be administered. The arrangement of the mouth guard 126 prevents direct skin to skin contact while still allowing air to pass from the person administering CPR to the patient receiving CPR via the apertures 127.

Method of Use

Figure 9:
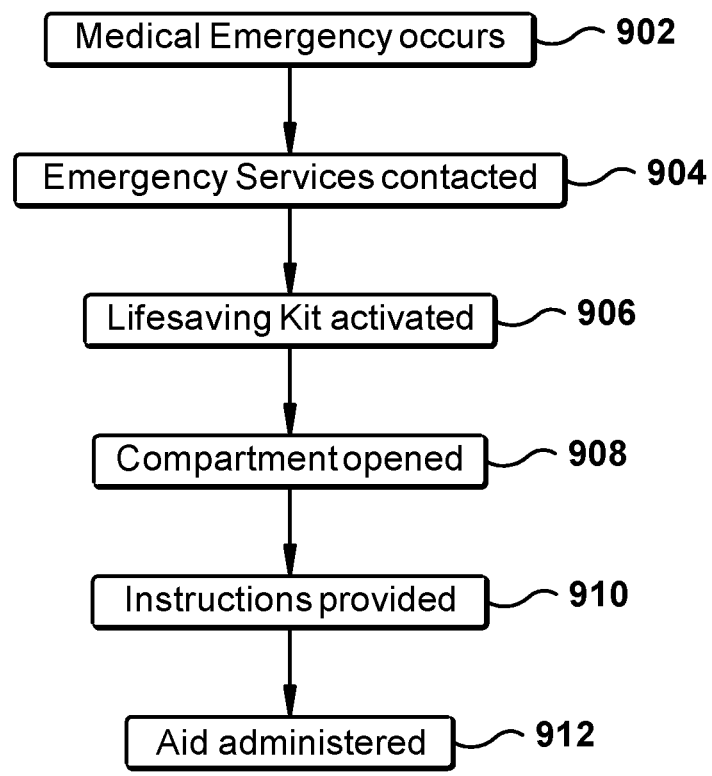
FIG. 9 is a flow diagram showing a method of using the kit of FIG. 1.

Referring to FIG. 9, a flow diagram explaining one exemplary use of the lifesaving kit is shown. At step 902 a medical emergency situation arises. For the purposes of this explanation, the medical emergency will be a patient who requires CPR due to drowning. At step 904, an operator contacts emergency services by dialing "9-1-1" or other appropriate emergency telephone number. At step 906, the operator activates the lifesaving kit by depressing the power button. At step 908, the operator opens the compartment that is appropriate for the medical emergency situation that has occurred. In the current example, the operator opens the first compartment 104 and retrieves the mouth guard 126. At step 910, the lifesaving kit provides verbal instructions via the speaker 140 on how to administer aid using the medical paraphernalia removed from the compartment based on which compartment has been opened by the operator. At step 912, the operator administers aid as instructed by the lifesaving kit 100 until emergency services arrive.

Although the above described use of the lifesaving kit is in regard to using the mouth guard to administer cardiopulmonary resuscitation, it is understood that a substantially similar process can be used to administer aid using one of the four other compartments, albeit with slight modifications. For example, if the medical emergency at step 902 is a stroke, then at step 908 the user will open the second compartment 106 and remove the aspirin contained therein. Then, at step 910, the lifesaving kit provides verbal instructions via the speaker on how to administer aid to the person suffering the stroke.

From the above description of the present disclosure, those skilled in the art will perceive improvements, changes and modifications. For example, the lifesaving kit can include an interface that allows an operator to specifically select the type of medical emergency encountered instead of relying on the opening of a particular compartment and the sensors. As another example, the lifesaving kit can include an interface that provides the estimated time until emergency services arrive. As yet another example, the lifesaving kit can be provided with a GPS tracker that assists the medical personnel in determining the precise location of the patient. Such improvements, changes, and modifications are within the skill of the art and are intended to be covered by the appended claims. All patents and patent applications identified herein are hereby incorporated by reference for all purposes.

The following is claimed:

1. An apparatus for providing medical aid comprising:
   a body configured for attachment to a cellular phone;
   a plurality of compartments disposed on the body and containing medical paraphernalia, each of the plurality of compartments having a closed condition and an open condition, one compartment of the plurality of compartments being separable from the remaining plurality of compartments and removed from the body and replaced with a replacement compartment once the medical paraphernalia is utilized; and
   an electronics system configured to provide instructions on how to utilize the medical paraphernalia.

2. The apparatus of claim 1, wherein the medical paraphernalia is at least one of a mouth guard, aspirin, glucose packets, personal medications, vitamins, and an epinephrine pen.

3. The apparatus of claim 1, further comprising a cover for each of the plurality of compartments, the cover selectively closing a respective one of the plurality of compartments and transitioning between the closed condition and the open condition, the cover being attached to the body by at least one of a pivotable connection, a slideable connection, a frangible connection, and perforations.

4. The apparatus of claim 3, further comprising a sensor that monitors whether the at least one of the plurality of compartments is in the closed condition or the open condition, the electronics system providing the auditory instructions when one of the plurality of compartments is in the open condition.

5. The apparatus of claim 1, further comprising an alarm that provides an operator programmable reminder that reminds an operator to administer the medical paraphernalia.

6. That apparatus of claim 3, wherein the cover is provided with indicia that identifies the contents of the respective compartment.

7. The apparatus of claim 1 further comprising a power button for activating the apparatus and a speaker for providing the instructions, the power button being movable relative to the speaker to selectively cover the speaker.

8. The apparatus of claim 1, wherein the body is integral with an external case of the cellular phone.

9. The apparatus of claim 1, wherein the instructions are auditory.

10. An apparatus for providing medical aid comprising:
    a body configured for attachment to a cellular phone;
    at least one compartment disposed on the body and containing at least one article of medical paraphernalia, the at least one compartment having a closed condition and an open condition;
    an electronics system configured to provide instructions on how to utilize the at least one article of medical paraphernalia; and
    an epinephrine pen that is pivotable relative to the body between an undeployed condition in which the epinephrine pen cannot be administered and a deployed condition in which the epinephrine pen can be administered.

11. An apparatus for providing medical aid consisting of:
    a body that is configured for attachment to a cellular phone;
    five compartments spaced along the body, a first compartment of the five compartments containing a mouth guard, a second compartment of the five compartments containing aspirin, a third compartment of the five compartments containing glucose packets, a fourth compartment of the five compartments containing at least one of personal medications and vitamins, and a fifth compartment of the five compartments containing an epinephrine pen, the fifth compartment being pivotable relative to the body between an undeployed condition in which the epinephrine pen cannot be administered and a deployed condition in which the epinephrine pen can be administered;

a separate cover associated with each of the five compartments, each of the covers being moveable relative to the body to transition a respective compartment between a closed condition and an open condition and having indicia that identifies the contents of the respective compartment of the five compartments; and an electronics system including a central processing unit, an electronic memory, and a speaker, the electronic memory storing lifesaving instructions, the central processing unit retrieving a particular set of lifesaving instructions based on a determination of which compartment is in the open condition, the speaker transforming the lifesaving instructions into a corresponding auditory instruction that can be heard by an operator.

\* \* \* \* \*